US008861824B2

(12) United States Patent
Nishimura

(10) Patent No.: US 8,861,824 B2
(45) Date of Patent: Oct. 14, 2014

(54) ULTRASONIC DIAGNOSTIC DEVICE THAT PROVIDES ENHANCED DISPLAY OF DIAGNOSTIC DATA ON A TOMOGRAPHIC IMAGE

(75) Inventor: Yushi Nishimura, Tokyo (JP)

(73) Assignee: Konica Minolta, Inc., Tokyo (JP)

( * ) Notice: Subject to any disclaimer, the term of this patent is extended or adjusted under 35 U.S.C. 154(b) by 0 days.

(21) Appl. No.: 13/320,775

(22) PCT Filed: Jul. 26, 2010

(86) PCT No.: PCT/JP2010/004750
§ 371 (c)(1),
(2), (4) Date: Nov. 16, 2011

(87) PCT Pub. No.: WO2011/013346
PCT Pub. Date: Feb. 3, 2011

(65) Prior Publication Data
US 2012/0063661 A1 Mar. 15, 2012

(30) Foreign Application Priority Data
Jul. 29, 2009 (JP) ................................. 2009-176041

(51) Int. Cl.
G06K 9/00 (2006.01)
A61B 8/00 (2006.01)
G06T 11/00 (2006.01)
G06T 7/00 (2006.01)

(52) U.S. Cl.
CPC . *A61B 8/00* (2013.01); *A61B 8/461* (2013.01); *G06T 2207/10132* (2013.01); *G06T 11/00* (2013.01); *G06T 2207/30048* (2013.01); *G06T 7/0081* (2013.01)
USPC ...................................................... 382/131

(58) Field of Classification Search
None
See application file for complete search history.

(56) References Cited

U.S. PATENT DOCUMENTS 4,614,196 A * 9/1986 Sato .............................. 600/443
5,873,830 A * 2/1999 Hossack et al. ............... 600/447
(Continued)

FOREIGN PATENT DOCUMENTS

CN 1496715 A 5/2004
CN 101461723 A 6/2009
(Continued)

OTHER PUBLICATIONS

Ito et al., Translation of Japanese Publication JP2006-141465, Originally Published Jun. 8, 2006, Cited in Chinese search report from Sep. 2013 provided in information disclosure statement on Nov. 15, 2013. Retrieved from Patent Abstracts of Japan, Date accessed Dec. 4, 2013.*
(Continued)

*Primary Examiner* — Tahmina Ansari
(74) *Attorney, Agent, or Firm* — Lucas & Mercanti, LLP

(57) ABSTRACT

An ultrasonic diagnostic apparatus is provided in which overlap of a displayed ultrasonic image and displayed diagnostic data can be avoided without imposing the burden of complicated operations on the operator.
An ultrasonic diagnostic apparatus includes: an ultrasonic probe for transmitting an ultrasonic beam to a tissue of a biological body and receiving a reflection wave of the ultrasonic beam reflected from the tissue; an image construction section for constructing an image frame of a first image representing a tomographic image of the tissue based on the reflection wave; an image analysis section for distinguishing a region of no interest based on an image feature quantity of the image frame, the region of no interest constituting part of the image frame which is exclusive of a region of interest that includes the tomographic image of the tissue; a data generation section for generating a second image that is for display of diagnostic data; an image synthesis section for generating a synthesized image by determining a display position of the second image based on a result of the distinguishment by the image analysis section and superimposing the second image on the image frame of the first image; and a display section for displaying the synthesized image.

7 Claims, 7 Drawing Sheets

(56) References Cited

U.S. PATENT DOCUMENTS

| | | | |
|---|---|---|---|
| 7,639,895 B2* | 12/2009 | Sakas et al. | 382/284 |
| 8,382,669 B2 | 2/2013 | Kakee | |
| 2004/0077946 A1 | 4/2004 | Ohmiya | |
| 2004/0254439 A1* | 12/2004 | Fowkes et al. | 600/407 |
| 2006/0257009 A1* | 11/2006 | Wang et al. | 382/128 |
| 2007/0073145 A1* | 3/2007 | Fan et al. | 600/437 |
| 2007/0167801 A1* | 7/2007 | Webler et al. | 600/459 |
| 2008/0118136 A1* | 5/2008 | Cai et al. | 382/131 |
| 2008/0249405 A1 | 10/2008 | Kakee | |
| 2009/0163815 A1* | 6/2009 | Kawagishi et al. | 600/453 |
| 2010/0030079 A1* | 2/2010 | Hamada | 600/443 |
| 2010/0033501 A1* | 2/2010 | Whitesell et al. | 345/634 |
| 2012/0063661 A1* | 3/2012 | Nishimura | 382/131 |
| 2012/0134562 A1* | 5/2012 | Boettger et al. | 382/131 |
| 2012/0148123 A1* | 6/2012 | Gindele | 382/128 |
| 2012/0150034 A1* | 6/2012 | DeFreitas et al. | 600/437 |

FOREIGN PATENT DOCUMENTS

| | | |
|---|---|---|
| JP | 59-032444 A | 2/1984 |
| JP | 05-329159 A | 12/1993 |
| JP | 07-194596 | 8/1995 |
| JP | 09-047453 A | 2/1997 |
| JP | 11-000326 A | 1/1999 |
| JP | 2001-017425 A | 1/2001 |
| JP | 2002-074328 | 3/2002 |
| JP | 2003-310602 | 5/2003 |
| JP | 2006-141465 A | 6/2006 |
| JP | 2007-185215 | 7/2007 |
| JP | 2008-253549 | 10/2008 |
| WO | WO 2008/081558 A1 * | 10/2008 |

OTHER PUBLICATIONS

Machida et al., Translation of Japanese Publication JP59032444, Originally Published Feb. 21, 1984, Cited in Chinese search report from Sep. 2013 provided in information disclosure statement on Nov. 15, 2013. Obtained from STIC Dec. 10, 2013.*

A. Masahiko, Medical Image Display Device, Japanese Patent Publication JP 2007-185215, Publication Date: Jul. 26, 2007, Cited by applicant in IDS submitted on Jul. 3, 2014. Translation retrieved using Patent Abstracts of Japan (PAJ) on Aug. 11, 2014. Copy Attached.*

International Search Report for corresponding International Application No. PCT/JP2010/004750 mailed Aug. 24, 2010.

Form PCT/ISA/237 for corresponding International Application No. PCT/JP2010/004750 dated Aug. 24, 2010 and Partial English translation.

Chinese Search Report with translation for corresponding Chinese Patent Application No. 201080033041.0 dated Sep. 30, 2013.

Japanese Office Action, Notice of Reasons for Rejection, Japanese Patent Application No. 2011-524655, drafting date: Jan. 10, 2014 (4 pages).

English translation of Japanese Office Action, Notice of Reasons for Rejection, Japanese Patent Application No. 2011-524655, drafting date: Jan. 10, 2014 (4 pages).

Japanese Office Action, Notice of Reasons for Rejection, Patent Application No. 2011-524655, Dispatch date: May 7, 2014 (3 double-sided pages).

English translation of Japanese Office Action, Notice of Reasons for Rejection, Patent Application No. 2011-524655, Dispatch date: May 7, 2014 (3 double-sided pages).

* cited by examiner

ULTRASONIC DIAGNOSTIC DEVICE THAT PROVIDES ENHANCED DISPLAY OF DIAGNOSTIC DATA ON A TOMOGRAPHIC IMAGE

TECHNICAL FIELD

The present invention relates to an ultrasonic diagnostic apparatus. More particularly, the present invention relates to a technique of displaying diagnostic data by an ultrasonic diagnostic apparatus.

BACKGROUND ART

The techniques of displaying diagnostic data so as not to overlap a region of interest in an ultrasonic image in an ultrasonic diagnostic apparatus are disclosed in Patent Document 1 and Patent Document 2.

Patent Document 1 discloses a technique of avoiding overlap of an ultrasonic image and diagnostic data, which is realized by preliminarily storing the display position of the ultrasonic image for every one of the bodies, diagnosed sites, or measurement functions and selecting a relevant one of the bodies, diagnosed sites, or measurement functions at the time of diagnosis.

Patent Document 2 discloses another technique of avoiding overlap of an ultrasonic image and diagnostic data, which is realized by an operator manually changing the vertical magnification rate, horizontal magnification rate, or display position of the text data region via a user interface.

CITATION LIST

Patent Literature

Patent Document 1: Japanese Laid-Open Patent Publication No. 11-326
Patent Document 2: Japanese Laid-Open Patent Publication No. 9-47453

SUMMARY OF INVENTION

Technical Problem

In diagnosis with the use of an ultrasonic diagnostic apparatus, an image is obtained through an ultrasonic probe which is in contact with a skin surface of a body. The position of the region of interest in the ultrasonic image may greatly vary depending on, for example, the angle of the probe or the posture of the body at the time of obtaining the image even if the same body or the same site is diagnosed. According to the aforementioned method disclosed in Patent Document 1, the display position of the diagnostic data is preliminarily stored and uniquely fixed. Therefore, the method of Patent Document 1 has difficulty in flexibly treating the variation of the position of the region of interest which may occur due to, for example, the angle of the probe or the posture of the body.

Using the method disclosed in Patent Document 2 enables change of the size of the display region of the diagnostic data and movement of the display position. However, these operations need to be manually carried out by an operator and are therefore complicated. Thus, they may disturb the concentration of the operator on the diagnosis.

The present invention was conceived for the purpose of solving the above problems. One of the objects of the present invention is to provide an ultrasonic diagnostic apparatus in which overlap of an ultrasonic image and diagnostic data can be avoided without imposing the burden of complicated operations on the operator.

Solution to Problem

An ultrasonic diagnostic apparatus of the present invention includes: an ultrasonic probe for transmitting an ultrasonic beam to a tissue of a biological body and receiving a reflection wave of the ultrasonic beam reflected from the tissue; an image construction section for constructing an image frame of a first image representing a tomographic image of the tissue based on the reflection wave; an image analysis section for distinguishing a region of no interest based on an image feature quantity of the image frame, the region of no interest constituting part of the image frame which is exclusive of a region of interest that includes the tomographic image of the tissue; a data generation section for generating a second image that is for display of diagnostic data; an image synthesis section for generating a synthesized image by determining a display position of the second image based on a result of the distinguishment by the image analysis section and superimposing the second image on the image frame of the first image; and a display section for displaying the synthesized image.

The image analysis section may divide the image frame into a plurality of small regions and calculate an image feature quantity of each of the small regions based on a luminance of the small region.

The image analysis section may calculate a mean value and a variance value of the luminance of each of the small regions and, and if both the mean value and the variance value are smaller than predetermined threshold values, the image analysis section may recognize the small region as being the region of no interest.

The image synthesis section may assign, as the display position of the second image, a region in the image frame which is recognized by the image analysis section as being the region of no interest, and generate the synthesized image.

The ultrasonic diagnostic apparatus may further include a user interface for an operator to instruct a change of the display position of the second image in the displayed synthesized image, wherein if the second region overlaps the region of interest as a result of the change of the display position of the second image which is instructed by the operator via the user interface, the image synthesis section forcedly changes the display position of the second image to a position in the region of no interest.

The image analysis section may continuously perform distinguishment of the region of no interest, and if the second region overlaps the region of interest as a result of movement of the region of interest within the image frame, the image synthesis section may change the display position of the second image to a position in a region which is presently recognized as the region of no interest.

The image synthesis section may hold a threshold value as to a distance between the second image and the region of interest across a display screen, and the image synthesis section may assign, as the display position of the second image, such a position that the distance between the second image and the region of interest which are displayed in the display section is smaller than the threshold value.

Advantageous Effects of Invention

According to the present invention, a region of no interest is distinguished based on an image feature quantity of an image frame, the region of no interest constituting part of the image frame which is exclusive of a region of interest that includes a tomographic image of a tissue. The display position of the second image that is to display diagnostic data is determined based on the distinguishment result, and a synthesized image is generated by superimposing the second image on an image frame of the first image. With this configuration, overlap of the ultrasonic image and the diagnostic data can be avoided without imposing the burden of complicated operations on the operator.

BRIEF DESCRIPTION OF DRAWINGS

FIG. 6(a) is a diagram of an example where the position of the region of interest moves from the initial position 604 to a position 602 in an image frame 600a so that the region of interest overlaps a diagnostic data image 603a. FIG. 6(b) is a diagram showing an image frame 600b where a diagnostic data image 603b is moved.

DESCRIPTION OF EMBODIMENTS

Hereinafter, an embodiment of an ultrasonic diagnostic apparatus of the present invention is described with reference to the attached drawings.

Figure 1:
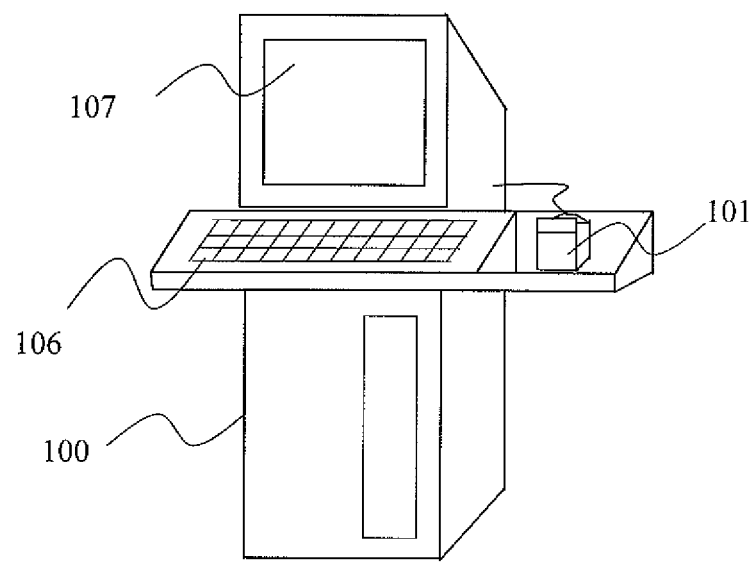
FIG. 1 is a diagram showing the exterior of an ultrasonic diagnostic apparatus 100 that is an embodiment of the present invention.

FIG. 1 shows the exterior of the ultrasonic diagnostic apparatus 100 of the present embodiment. The ultrasonic diagnostic apparatus 100 displays in real time on a monitor 107 a tomographic image of an internal tissue which is produced using an ultrasonic probe 101. In that case, an image which shows the diagnostic data of a subject, for example, is superimposed on an image frame of the tomographic image and displayed on the monitor 107. Note that this "diagnostic data" comprehensively represents information about the subject and information about the diagnostic apparatus used and the diagnostic procedure.

The ultrasonic diagnostic apparatus 100 of the present embodiment determines the display position of the image that shows the diagnostic data, or the like, according to a distinguishment result as to whether it is a region of the image frame in which a tomographic image of a tissue is present (region of interest) or the other region of the image frame which is exclusive of the region of interest (region of no interest), and superimposes the image on the image frame. More specifically, the ultrasonic diagnostic apparatus 100 superimposes an image which shows the diagnostic data, or the like, on the region of no interest of the image frame.

In the description below, the configuration of the ultrasonic diagnostic apparatus 100 is first described, and then, how the ultrasonic diagnostic apparatus 100 specifies a region of no interest and in what manner an image which shows, for example, data about the subject is superimposed on the specified region of no interest are described in detail.

Figure 2:
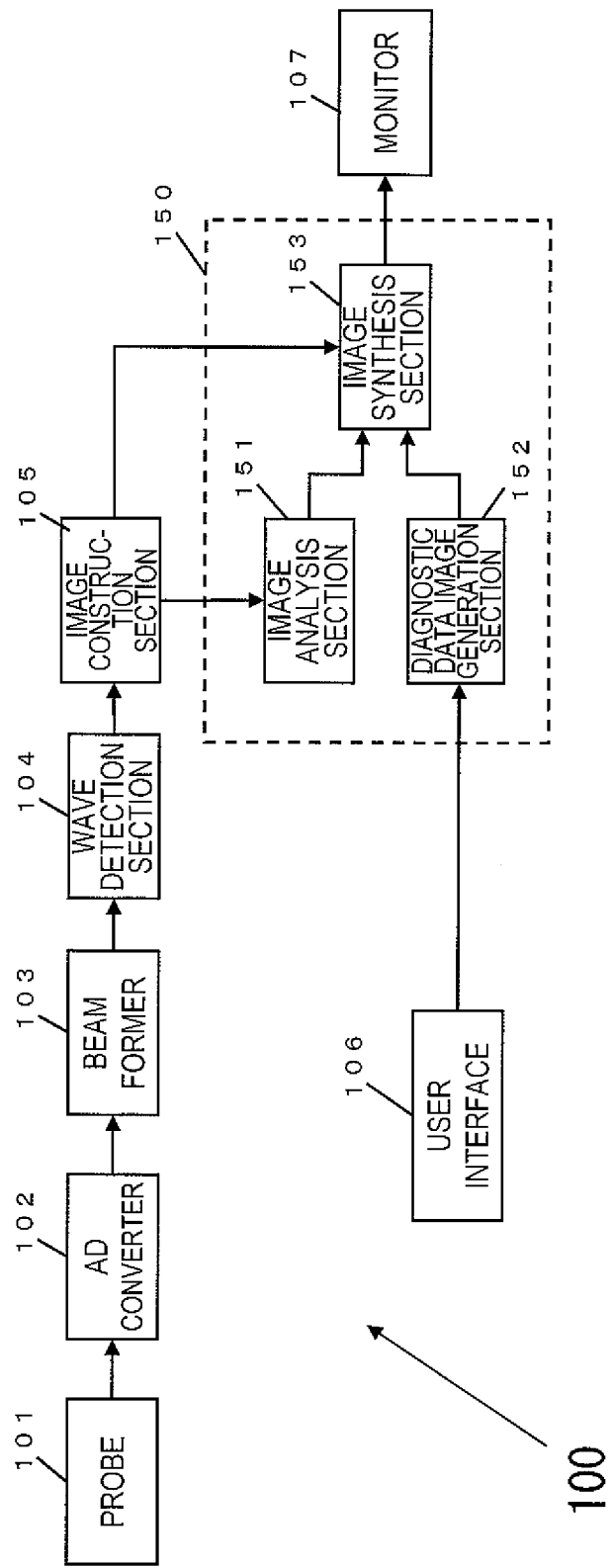
FIG. 2 is a block diagram showing one configuration example of the ultrasonic diagnostic apparatus 100 that is an embodiment of the present invention.

FIG. 2 is a block diagram showing a configuration example of the ultrasonic diagnostic apparatus 100 of the present embodiment.

The ultrasonic diagnostic apparatus 100 includes a probe 101, an AD converter 102, a beam former 103, a wave detection section 104, an image construction section 105, a user interface 106, a monitor 107, and a processor 150.

The ultrasonic probe 101 transmits and receives an ultrasonic beam. During the operation of the ultrasonic diagnostic apparatus 100, the ultrasonic probe 101 transmits an ultrasonic beam to a tissue of a biological body and receives a reflection wave of the ultrasonic beam from the tissue of the biological body.

The AD converter 102 converts the received ultrasonic reflection wave to a digital signal. The beam former 103 performs delayed combination on the AD-converted ultrasonic reflection wave. The wave detection section 104 performs envelope detection on an ultrasonic echo signal obtained by the delayed combination.

The image construction section 105 performs a signal process on a detected ultrasonic echo signal to construct a tomographic image frame of the tissue.

The user interface 106 is an entry device, such as a keyboard, which is utilized by an operator for entering diagnostic data (e.g., data about a subject) or data other than the diagnostic data (non-diagnostic data). Note that the user interface 106 may be utilized when instructing whether or not data is displayed on the monitor 107 or when instructing a change of the display position of displayed data. For example, when the operator instructs a change of the display position of a diagnostic data image which will be described later, the user interface 106 may be utilized.

The monitor 107 may be a display device in which, for example, a liquid crystal or a cathode ray tube is used, and which is configured to display an ultrasonic image and an image of the diagnostic data.

Note that a touchscreen into which the user interface 106 and the monitor 107 are integrated may be provided.

The processor 150 is a so-called central processing unit (CPU) and is configured to analyze an image frame of a tomographic image (ultrasonic image) and determine the display position of the diagnostic data and/or non-diagnostic data.

The processor 150 includes an image analysis section 151 for analyzing an ultrasonic image, a diagnostic data image generation section 152 for generating an image of the diagnostic data, and an image synthesis section 153 for synthesizing the ultrasonic image and the diagnostic data. Each of these components may be configured by hardware or may be configured by software running on the processor 150 to carry out the function of the component.

When the processor 150 is, for example, a special-purpose integrated circuit chip which is designed and manufactured exclusively for the ultrasonic diagnostic apparatus 100, the image analysis section 151, the diagnostic data image generation section 152 and the image synthesis section 153 are configured as independent integrated circuits in the processor 150.

When the processor 150 is a general-purpose integrated circuit chip, the image analysis section 151, the diagnostic data image generation section 152 and the image synthesis section 153 are realized by the processor 150 and computer programs executed by the processor 150. Specifically, suppose that there are library programs A, B and C provided for implementing the respective functions of the image analysis section 151, the diagnostic data image generation section 152 and the image synthesis section 153. During the execution of the library program A, the processor 150 functions as the image analysis section 151. During the execution of the library program B, the processor 150 functions as the diagnostic data image generation section 152. The same applies to the other program. Note that the processor 150 may execute the plurality of programs in parallel, so that the processor 150 seemingly concurrently operates as the image analysis section 151, the diagnostic data image generation section 152 and the image synthesis section 153.

Next, an operation of the ultrasonic diagnostic apparatus 100 is described.

Figure 3:
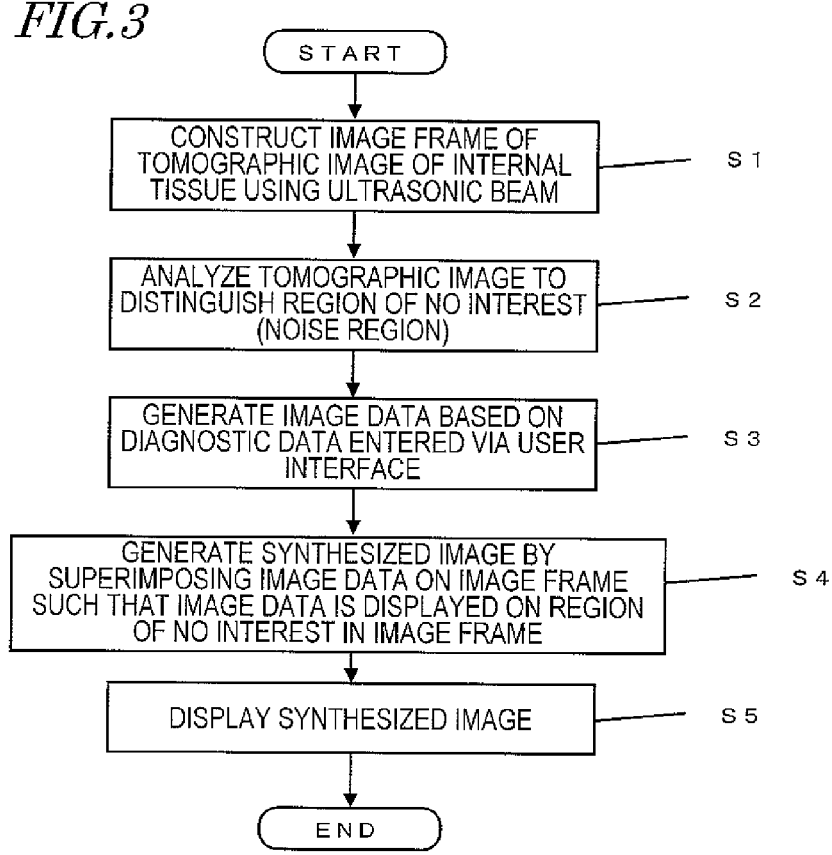
FIG. 3 is a flowchart illustrating the operation procedure of the ultrasonic diagnostic apparatus 100.

FIG. 3 is a flowchart which illustrates the procedure in the ultrasonic diagnostic apparatus 100.

In step S1, the ultrasonic diagnostic apparatus 100 constructs an image frame of a tomographic image of an internal tissue with the use of an ultrasonic beam of the probe 101. Specifically, the probe 101 transmits an ultrasonic beam into a biological body and receives a reflection wave of the ultrasonic beam from a tissue inside the biological body, for example. The AD converter 102 converts the received reflection wave of the ultrasonic beam to a digital signal. The beam former 103 performs a delayed combination process on the digital signal. The wave detection section 104 performs envelope detection to remove a transmitted wave (carrier) component from the received signal. The resultant signal is input to the image construction section 105. The image construction section 105 performs a filtering process, a luminance conversion process, a scan line conversion (scan convert) process, etc., on the input ultrasonic echo signal to construct an ultrasonic tomographic image frame. The ultrasonic tomographic image frame is output to the processor 150. The image frame is first input to the image analysis section 151 in the processor 150.

In step S2, the image analysis section 151 analyzes the tomographic image to distinguish a noise region in the image frame. The "noise region" means a region of the image frame which is exclusive of the region that includes the image of the internal tissue. In the specification of the present application, the noise region is referred to as "region of no interest". Part of the image of the internal tissue which is utilized by an operator for diagnosis, or which is adopted as the basis for diagnosis, is referred to as "region of interest" or "non-noise region". The process of distinguishing the noise region will be described later in detail with reference to FIG. 8.

Then, in step S3, the diagnostic data image generation section 152 generates image data based on the diagnostic data entered via the user interface.

First, the operator uses the user interface 106 to perform measurements of the image, etc., and enter the diagnostic data. The diagnostic data image generation section 152 converts the entered diagnostic data to image data. This process is, for example, conversion of the diagnostic data entered in the form of text data to an image object. The diagnostic data converted to an image object is hereinafter referred to as "diagnostic data image".

In step S4, the image synthesis section 153 generates a synthesized image by superimposing the diagnostic data image on the image frame (or synthesizing the diagnostic data image with the image frame) such that the diagnostic data image is displayed on the noise region (region of no interest) in the image frame. Determination as to whether or not the diagnostic data image is on the noise region in the image frame may be made based on whether or not, supposing that the diagnostic data image is rectangular, the entire area of the rectangular image is within the noise region 501.

Figure 4:
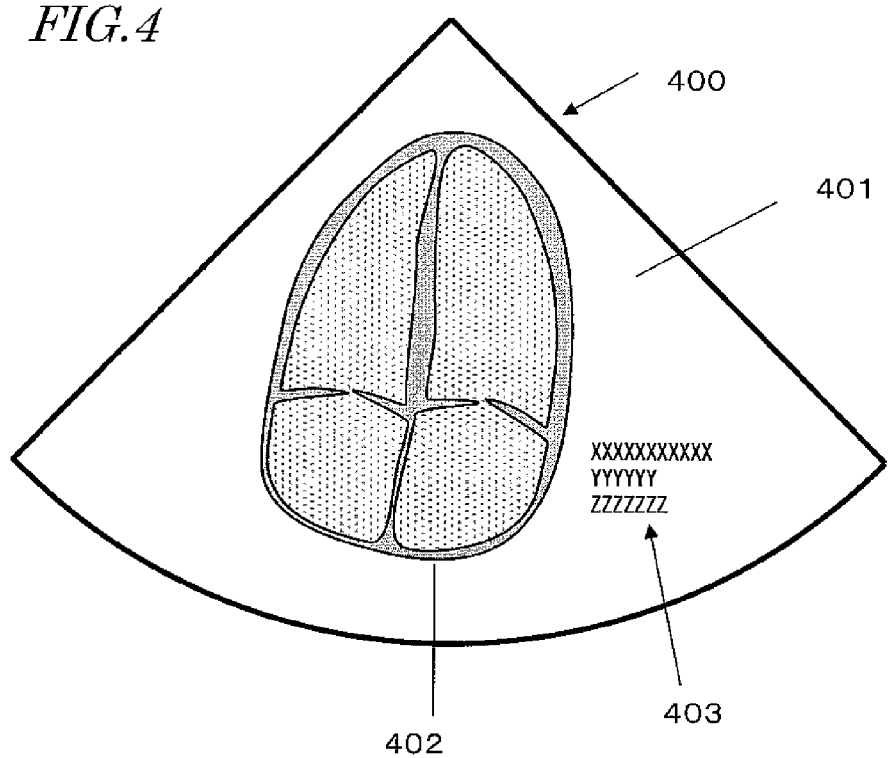
FIG. 4 is a diagram showing a synthesized image 400 displayed on a monitor 107.

In step S5, the monitor 107 displays the synthesized image. FIG. 4 shows the synthesized image 400 displayed on the monitor 107. The synthesized image 400 includes a noise region 401 and a non-noise region 402. A diagnostic data image 403 is displayed in the noise-region 401.

When the diagnostic data image 403 is displayed on a region of no interest, the display position of the diagnostic data image 403 is preferably as close to a region of interest as possible. This is for the purpose of minimizing the movement of the sight line of the operator. For example, in the case where the blood vessel wall of the common carotid artery is observed and the intima-media thickness measured, the measured values are preferably displayed in part of the region of no interest which is close to the blood vessel wall.

Thus, the image synthesis section 153 may generate a synthesized image such that the diagnostic data image is placed at such a position that the distance between the diagnostic data image and the region of interest is smaller than a predetermined threshold value. The operator can preset the threshold value in the image synthesis section 153 via the user interface 106. The image synthesis section 153 holds the threshold value in, for example, an internal memory, and refers to the threshold value in determination of where on the region of no interest the diagnostic data image 403 is to be displayed.

Figure 6:
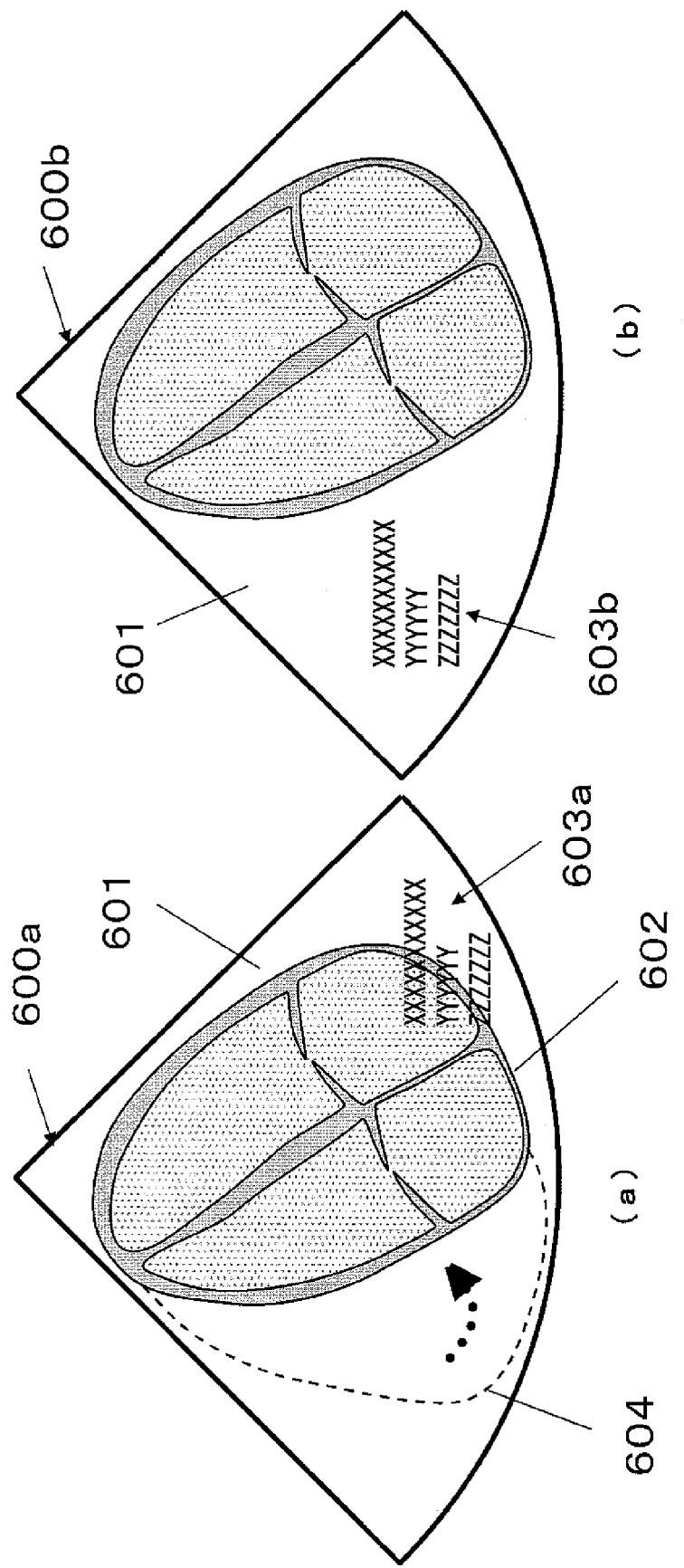

In the present embodiment, even after the above process is completed, the image analysis section 151 continues the process of distinguishing the noise region as described above as long as generation of ultrasonic images is continued. This is because the positions of the region of interest and the region of no interest may vary depending on, for example, the position of the probe 101. The process performed in this phase will be described later with reference to FIG. 6.

Hereinafter, a specific example is described.

Figure 5:
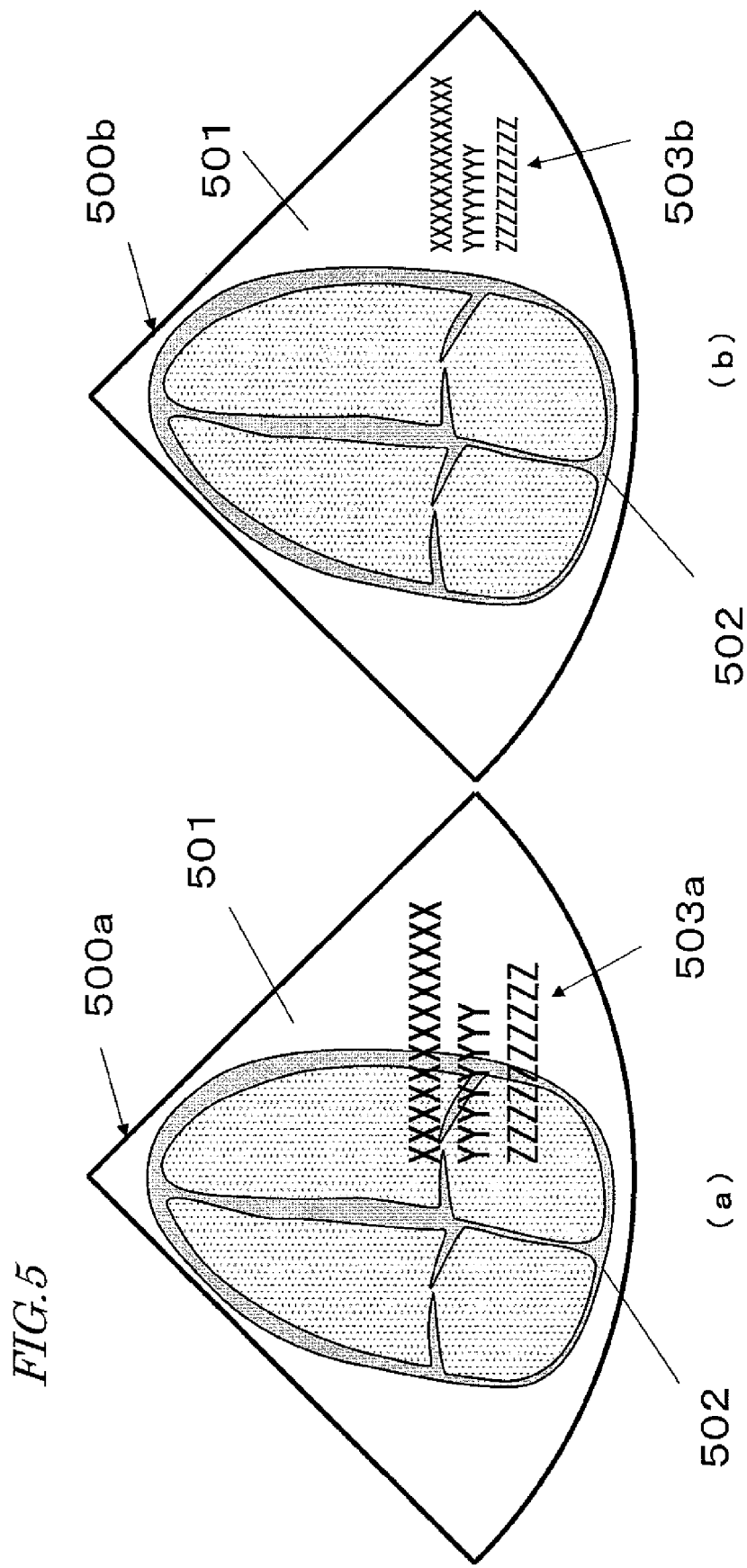
FIG. 5(a) is a diagram showing an image 500a where the arrangement of a diagnostic data image 503a is not adjusted.
FIG. 5(b) is a diagram showing an image 500b where a downsized diagnostic data image 503b is displayed.

FIG. 5(*a*) shows an image 500*a* where the arrangement of a diagnostic data image 503*a* is not adjusted. In the image 500*a*, the diagnostic data image 503*a* is displayed in a predetermined size at a predetermined position. As shown, part of the diagnostic data image 503*a* lies over the noise region 501 while the other part lies over a region of interest 502. In this example, the diagnostic data region is unduly large so that it cannot be displayed without overlapping the region of interest.

In that case, the image synthesis section 153 displays a diagnostic data image 503*b*, which is a downsized version of the diagnostic data image 503*a*, as shown in FIG. 5(*b*). The image synthesis section 153 downsizes the diagnostic data image stepwise and determines, at every step of downsizing, whether or not the downsized diagnostic data image can be displayed within the noise region 501. This determination is similar to the previously-described determination as to whether or not the diagnostic data image is present on the noise region in the image frame. If the diagnostic data image is rectangular, the determination may be made based on whether or not all the vertexes at the four corners of the rectangular image are in the noise region 501. In this way, a synthesized image 500*b*, in which the diagnostic data image 503*b* is placed on the noise region 501 that is different from the region of interest 502, can be displayed.

FIG. 6(a) shows an example where the position of the region of interest moves from the initial position 604 to a position 602 in an image frame 600a so that the region of interest overlaps a diagnostic data image 603a. Such a move of the region of interest may occur due to, for example, a variation of the angle of the probe 101 or the posture of the body.

In this situation, the image synthesis section 153 can automatically move the diagnostic data image 603b to a position shown in FIG. 6(b). The image synthesis section 153 analyzes the image 600a after the move of the region of interest to distinguish a noise region 601 again. Then, the diagnostic data image may be superimposed on the image frame such that the diagnostic data image is displayed on the distinguished noise region. In this way, a synthesized image 600b shown in FIG. 6(b) can be obtained.

Figure 7:
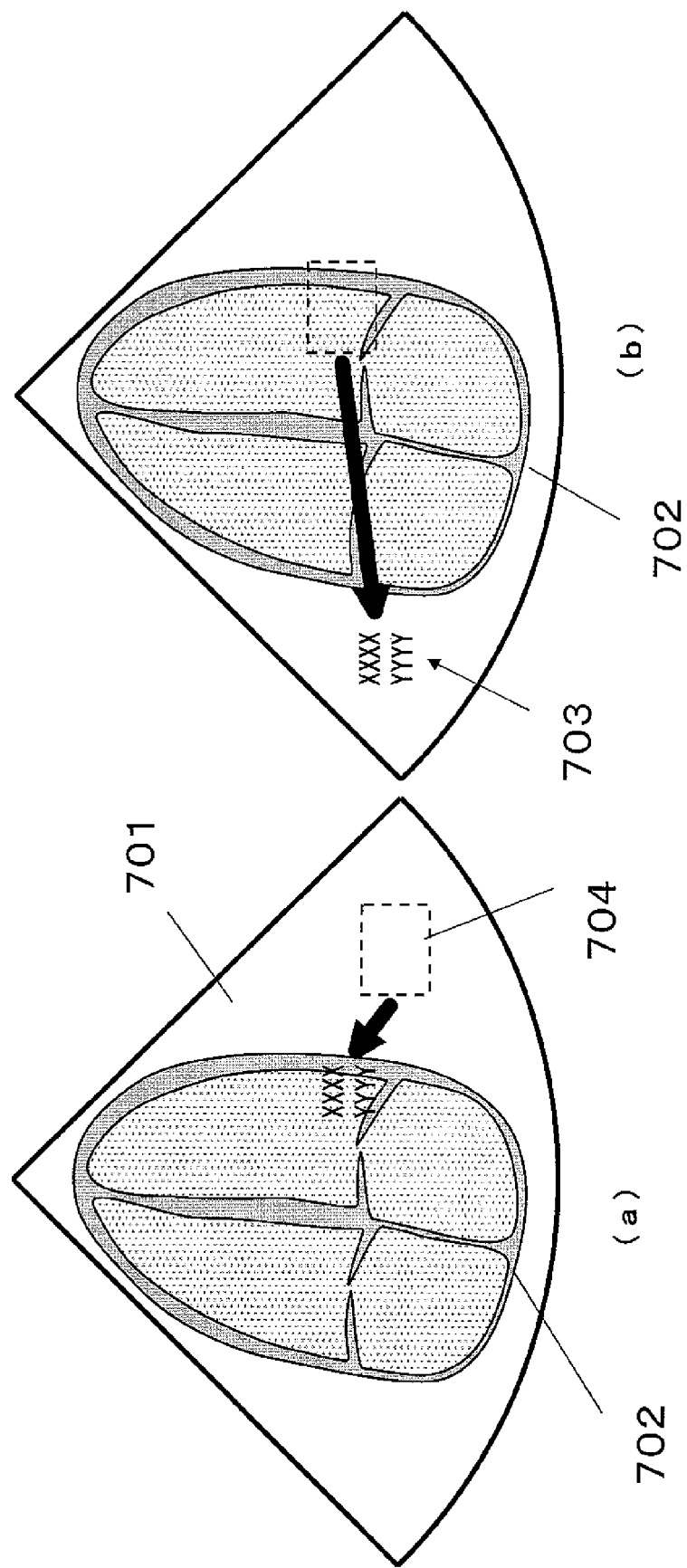
FIG. 7(a) is a diagram of an example where an operator instructs via a user interface 106 to move a diagnostic data image from the initial position 704 in a noise region 701 to a position in the region of interest 702.
FIG. 7(b) is a diagram showing a forcedly-moved diagnostic data image 703.

Also, the operator can move the display position of the diagnostic data using the user interface 106. FIG. 7(a) shows an example where the operator attempts to move the diagnostic data image from the initial position 704 in a noise region 701 to a position on the region of interest 702 via a user interface 106. In such a situation, the image synthesis section 153 of the processor 501 can automatically (or "forcedly") move the diagnostic data image to a position on the noise region 702 as shown in FIG. 7(b).

Figure 8:
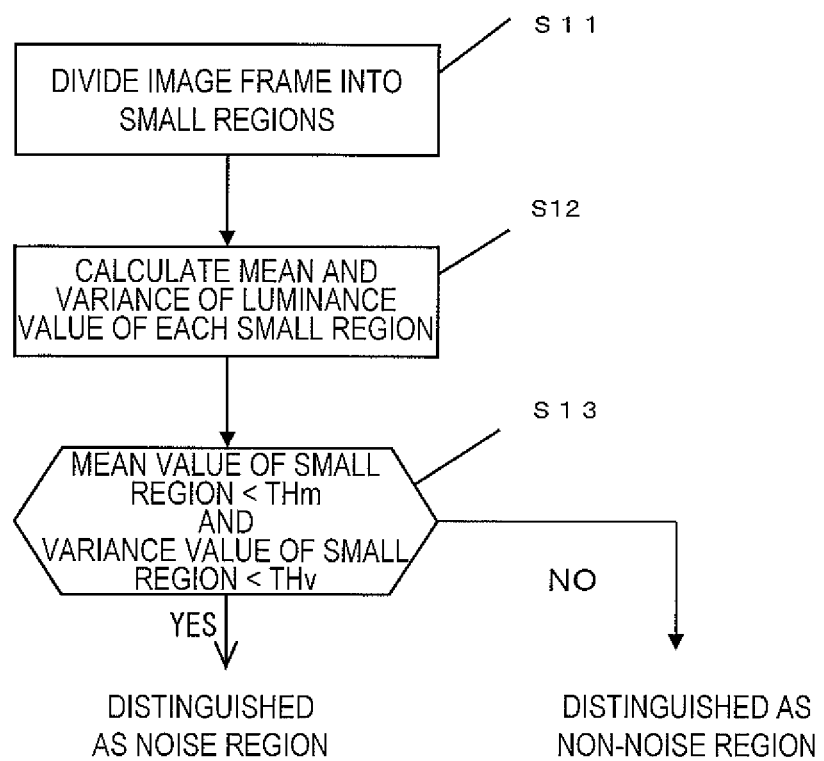
FIG. 8 is a flowchart illustrating the operation procedure of detecting a noise region.

Next, a method of detecting a noise region, which is implemented by the image analysis section 151, is described. FIG. 8 is a flowchart illustrating the operation procedure of detecting a noise region. First, in step S11, the image analysis section 151 divides the image frame into small regions. In the subsequent step S12, the image analysis section 151 calculates the mean value and the variance value of the luminance of each of the small regions. In the specification of the present application, these physical quantities are also referred to as "image feature quantities".

In the subsequent step S13, the image analysis section 151 determines whether or not the mean value and the variance value of each of the small regions are smaller than threshold values THm and THv, respectively. The mean value and the variance value of the luminance of the noise component have a tendency to be smaller than those of the luminance of the biological body tissue component. Therefore, if the mean value and the variance value of each of the small regions are smaller than the predetermined threshold values THm and THv, respectively, the small region is estimated to be a noise region. On the other hand, if that condition is not met, the small region is estimated to be a non-noise region (region of interest). Therefore, by determination which is made based on the above criteria, it can be distinguished whether the small region is a noise region or a region of interest. Note that the size of the small region can be arbitrarily determined, although it is desirably equal to the size of the diagnostic data image generated by the diagnostic data image generation section 152. Note that the threshold values THm and THv can be determined as a function of the mean luminance and the variance of the entire image. Note that the threshold values may vary depending on the noise level of the ultrasonic diagnostic apparatus 100, the site which is to undergo diagnosis, and the parameters set by a user (such as dynamic range, transmission power, etc.) Therefore, appropriate values may be determined through adjustments on the ultrasonic diagnostic apparatus 100.

According to the above process, whether or not each of the small regions is a noise region can be determined based on the image feature quantities. By making the determination on every one of the small regions, the region of interest that includes an image corresponding to the internal tissue and the noise region can be distinguished with the accuracy which depends on the size of the small region.

In this example, a noise region is detected as a region of no interest, although there is a region of no interest other than the noise region. Even in such a case, the region of no interest can be detected using a variety of methods other than the method illustrated in FIG. 8. For example, it is highly probable that part of the image which frequently moves is a region of interest, and therefore, a method of distinguishing a region of no interest from a region of interest by means of motion detection which is based on the frame correlation may be applicable.

When the shape and the luminance pattern of the region of interest are specified beforehand, such as in the case of measurement of the intima-media thickness of the blood vessel wall of the common carotid artery, the image analysis section 151 may detect the region of interest by means of pattern matching, thereby distinguishing the region of interest and the region of no interest from each other.

In this example, the tomographic image (B mode) is described, although the extent of the present invention is not limited to the B mode. As a matter of course, the present invention is applicable to typical ultrasonic images of other types, such as M mode, Doppler mode, etc.

In the above-described embodiment, the user himself enters the diagnostic data using the user interface 106. However, the "diagnostic data" is merely an example. For example, non-diagnostic data which is irrelevant to diagnosis (e.g., the name of the subject, the date of production of the tomographic image, etc.) may be entered. Further, the user interface 106 may not be used in entering the diagnostic data or non-diagnostic data. The diagnostic data or non-diagnostic data may be produced by the processor 150. For example, the processor 150 may measure and display the thickness of the tissue in a tomographic image.

The procedure which has been previously described using the flowchart shown in FIG. 3 may be implemented in the form of a computer program which is executed by the image construction section 105 and the processor 150. Such a computer program may be recorded in a storage medium, such as CD-ROM, which is to be circulated as a commercial product in the market, or may be distributed via electric communication lines, such as the Internet. Note that, the functions of the image construction section 105 may be realized by the processor 150 which executes computer programs, instead of providing the image construction section 105 as hardware.

INDUSTRIAL APPLICABILITY

An ultrasonic diagnostic device of the present invention can display various diagnostic data concerning a body so as not to overlap a region of interest of an ultrasonic image and is therefore useful to, for example, medical applications.

REFERENCE SIGNS LIST 101 probe
102 AD converter
103 beam former
104 wave detection section
105 image construction section
106 user interface
107 monitor
150 processor
151 image analysis section
152 diagnostic data image generation section
153 image synthesis section

The invention claimed is:

1. An ultrasonic diagnostic apparatus, comprising:
an ultrasonic probe configured to transmit an ultrasonic beam to a tissue of a biological body and receiving a reflection wave of the ultrasonic beam reflected from the tissue;
circuitry configured:
to construct an image frame of a first image representing a tomographic image of the tissue based on the reflection wave, wherein the first image contains a region of interest including the tomographic image of the tissue and a region of no interest exclusive of the region of interest that includes the tomographic image of the tissue;
to perform a distinguishment of the region of no interest based on an image feature quantity of the image frame wherein the image feature quantity is based on a luminance of the region;
to generate a second image that is for display of diagnostic data represented by text; and
to generate a synthesized image by determining a display position of the second image based on a result of the distinguishment and superimposing the second image on the image frame of the first image; and
a display configured to display the synthesized image.

2. The ultrasonic diagnostic apparatus of claim 1, wherein the circuitry is configured to perform image analysis by dividing the image frame into a plurality of small regions and by calculating an image feature quantity of each of the small regions based on the luminance of the small region.

3. The ultrasonic diagnostic apparatus of claim 2, wherein the circuitry is configured to perform the image analysis by calculating a mean value and a variance value of the luminance of each of the small regions, and
if both the mean value and the variance value are smaller than predetermined threshold values, the image analysis performed by the circuitry recognizes the small region as being the region of no interest.

4. The ultrasonic diagnostic apparatus of claim 1, wherein the circuitry is configured to perform the image synthesis by assigning, as the display position of the second image, a region in the image frame which is recognized by the circuitry as being the region of no interest, and to generate the synthesized image.

5. The ultrasonic diagnostic apparatus of claim 1, further comprising a user interface for an operator to instruct a change of the display position of the second image in the displayed synthesized image,
wherein if the second region overlaps the region of interest as a result of the change of the display position of the second image which is instructed by the operator via the user interface, the image synthesis performed by the circuitry forcedly changes the display position of the second image to a position in the region of no interest.

6. The ultrasonic diagnostic apparatus of claim 1, wherein the circuitry is configured to perform image analysis by continuously performing distinguishment of the region of no interest, and
if the second region overlaps the region of interest as a result of movement of the region of interest within the image frame, the image synthesis performed by the circuitry changes the display position of the second image to a position in a region which is presently recognized as the region of no interest.

7. The ultrasonic diagnostic apparatus of claim 1, wherein the circuitry is configured to perform the image synthesis by holding a threshold value as to a distance between the second image and the region of interest across a display screen, and
the circuitry is configured to perform the image synthesis by assigning, as the display position of the second image, such a position that the distance between the second image and the region of interest which are displayed in the display is smaller than the threshold value.

* * * * *